(12) United States Patent
Khodak et al.

(10) Patent No.: US 8,821,368 B2
(45) Date of Patent: Sep. 2, 2014

(54) WARMING THERAPY DEVICE INCLUDING MODULAR HUMIDIFICATION SYSTEM

(75) Inventors: Elena Khodak, Hatfield, PA (US); Peter D. Sabota, Warminster, PA (US); Robert J. Chilton, III, Quakertown, PA (US); Dan Dolan, Perkasie, PA (US)

(73) Assignee: Draeger Medical Systems, Inc., Telford, PA (US)

( * ) Notice: Subject to any disclaimer, the term of this patent is extended or adjusted under 35 U.S.C. 154(b) by 581 days.

(21) Appl. No.: 13/062,432

(22) PCT Filed: Sep. 22, 2009

(86) PCT No.: PCT/US2009/057784
§ 371 (c)(1),
(2), (4) Date: Mar. 4, 2011

(87) PCT Pub. No.: WO2010/036635
PCT Pub. Date: Apr. 1, 2010

(65) Prior Publication Data
US 2011/0172487 A1    Jul. 14, 2011

Related U.S. Application Data (60) Provisional application No. 61/101,001, filed on Sep. 29, 2008, provisional application No. 61/101,014, filed on Sep. 29, 2008, provisional application No. 61/101,025, filed on Sep. 29, 2008, provisional application No. 61/100,967, filed on Sep. 29, 2008, provisional application No. 61/100,994, filed on Sep. 29, 2008.

(51) Int. Cl.
*A61G 11/00* (2006.01)
*A61M 16/10* (2006.01)
*A61F 7/00* (2006.01)
*A61M 16/16* (2006.01)

(52) U.S. Cl.
CPC ........ *A61G 11/00* (2013.01); *A61M 2205/3653* (2013.01); *A61F 2007/0062* (2013.01); *A61G 2203/46* (2013.01); *A61M 16/16* (2013.01); *A61M 16/109* (2014.02); *A61G 11/009* (2013.01)
USPC .......................................................... 600/22

(58) Field of Classification Search
USPC .............................. 600/21–22; 392/403; 5/655
See application file for complete search history.

(56) References Cited

U.S. PATENT DOCUMENTS

| | | | |
|---|---|---|---|
| 5,242,375 A * | 9/1993 | McDonough .................... 600/22 |
| 6,024,694 A * | 2/2000 | Goldberg et al. ................ 600/22 |
| 6,711,937 B2 | 3/2004 | Richards et al. ............. 73/29.01 |
| 7,674,223 B2 * | 3/2010 | Jones ............................... 600/22 |
| 2001/0049465 A1 * | 12/2001 | Goldberg et al. ................ 600/22 |
| 2004/0234254 A1 * | 11/2004 | Czupich et al. ................. 392/403 |

FOREIGN PATENT DOCUMENTS

| WO | 99/12513 A1 | 3/1999 | ............. A61G 11/00 |
|---|---|---|---|
| WO | 03/043560 A2 | 5/2003 | ............. A61G 11/00 |

* cited by examiner

*Primary Examiner* — Christine Matthews
(74) *Attorney, Agent, or Firm* — DLA Piper LLP (US)

(57) ABSTRACT

An apparatus and method for performing warming therapy is described. In one exemplary embodiment, the apparatus includes a base for supporting a medical patient and a humidifier module removably coupled to the base. The humidifier module may include a main reservoir and an evaporator reservoir separated by a channel. Both the main and evaporator reservoirs may be protected by a cover, which may be made removable. The design of the humidifier module is such that the component parts thereof may be easily removed, so that the reservoir body including the main reservoir and the evaporator reservoir may be easily cleaned, such as through use of an autoclave.

9 Claims, 12 Drawing Sheets

WARMING THERAPY DEVICE INCLUDING MODULAR HUMIDIFICATION SYSTEM

CROSS REFERENCE TO RELATED APPLICATIONS

This application is a §371 of International Application No. PCT/US09/57784, filed Sep. 22, 2009 (WO 2010/036635, published Apr. 1, 2010), which claims priority to U.S. Provisional Application Ser. No. 61/101,001, filed Sep. 29, 2008, U.S. Provisional Application Ser. No. 61/101,014, filed Sep. 29, 2008, U.S. Provisional Application Ser. No. 61/101,025, filed Sep. 29, 2008, U.S. Provisional Application Ser. No. 61/100,967, filed Sep. 29, 2008, and U.S. Provisional Application Ser. No. 61/100,994, filed Sep. 29, 2008, the entire contents of which are hereby incorporated by reference, as if fully set forth herein.

FIELD OF THE INVENTION

This present invention relates generally to a method and apparatus for performing warming therapy on medical patients. More particularly, the present invention relates to a method and apparatus for humidifying air supplied to a medical patient disposed within an enclosure.

BACKGROUND OF THE INVENTION

It is known to control both the temperature and relative humidity of the air adjacent a medical patient (e.g., infant) in a warming therapy device. For example, many warming therapy devices (e.g., incubators, warmers, etc.) include systems which are designed to control the temperature and humidity of the environment surrounding an infant patient disposed inside a hood of the warming therapy device. To control the temperature and humidity within the warming therapy device, the existing temperature and humidity are sensed and then adjusted. The temperature within the warming therapy device may be adjusted using a heating element located within the air circulation system of the warming therapy device and responsive to a temperature sensor. The humidity within a warming therapy device may be adjusted using a humidification device that is adapted to inject humidity into the air circulation system of the warming therapy device.

Humidification systems typically comprise at least a water reservoir and a heating element. The heating element typically acts to heat the water within the reservoir, and thus create humidity by adding water vapor to heated air. Humidification systems often require cleaning, such as by inserting the device in an autoclave. In this respect, it is desirable to implement an easily removable, efficient design of a humidification system, while providing the functionality and accuracy of more complex systems. Further, humidification systems are often re-filled with water, and/or checked for water volume while an infant patient is disposed within the respective warming therapy device. Thus, it is desirable to provide a humidification system that is easy to fill and/or service without disturbing the infant patient.

As noted above, humidification systems of conventional warming therapy devices (such as the ones discussed above) are often difficult to clean, due to the way in which they are integrated into the warming therapy devices. For example, many portions of the humidification systems are often built into the base of the respective warming therapy device, and thus are difficult (and sometimes impossible) to disassemble and clean. Because one of the objectives of a warming therapy device is to create a sterile and hygienically sound environment for the patient, a humidification system which may be easily disassembled and cleaned by autoclave is highly desirable.

Accordingly, there is presently a need for a warming therapy device that includes a modular humidification system which may be easily disassembled and cleaned by autoclave.

SUMMARY OF THE INVENTION

An exemplary embodiment of the present invention comprises an apparatus including a base for supporting a medical patient and a humidifier module removably coupled to the base, the humidifier module including a main reservoir and an evaporator reservoir separated by a channel.

An exemplary embodiment of the present invention also comprises a humidifier module including a reservoir body and a cover adapted to cover a portion of the reservoir body, wherein the reservoir body comprises a main reservoir and an evaporator reservoir separated by a channel.

An exemplary embodiment of the present invention also comprises an apparatus including a base for supporting a medical patient, a pedestal supporting the base, a hood surrounding a portion of the base and a humidifier module coupled to the base, the humidifier module including a reservoir body and a cover adapted to cover a portion of the reservoir body, wherein the reservoir body comprises a main reservoir and an evaporator reservoir separated by a channel.

DETAILED DESCRIPTION

The present invention relates to a warming therapy device (e.g., incubator, warmer, etc.) including a modular humidification system which allows easy cleaning of the system. In particular, the warming therapy device includes a mattress tray assembly which may be coupled to a humidification system formed of various component parts which may be easily assembled and disassembled for cleaning purposes.

By way of example, the humidification system according to the exemplary embodiments of the present invention may be used in connection with an incubator and humidity sensor such as are disclosed and discussed in U.S. Pat. No. 6,711,937 (assigned to the same assignee as the present application), which is hereby incorporated by reference in its entirety, as if fully set forth herein. For example, U.S. Pat. No. 6,711,937 describes an incubator 26 having a base 11 into which a humidifier module 23 may be inserted. The incubator 26 also includes a sensor module 10 for sensing conditions such as temperature and humidity within the incubator, and providing control signals for regulating the same. However, the humidifier module 23 suffers from several drawbacks, including that it may not be easily disassembled and cleaned (using an autoclave, for example). The present invention avoids many of the drawbacks of conventional humidifier modules by making the structure modular in nature, such that individual elements may be easily removed, cleaned and re-inserted.

Figure 1:
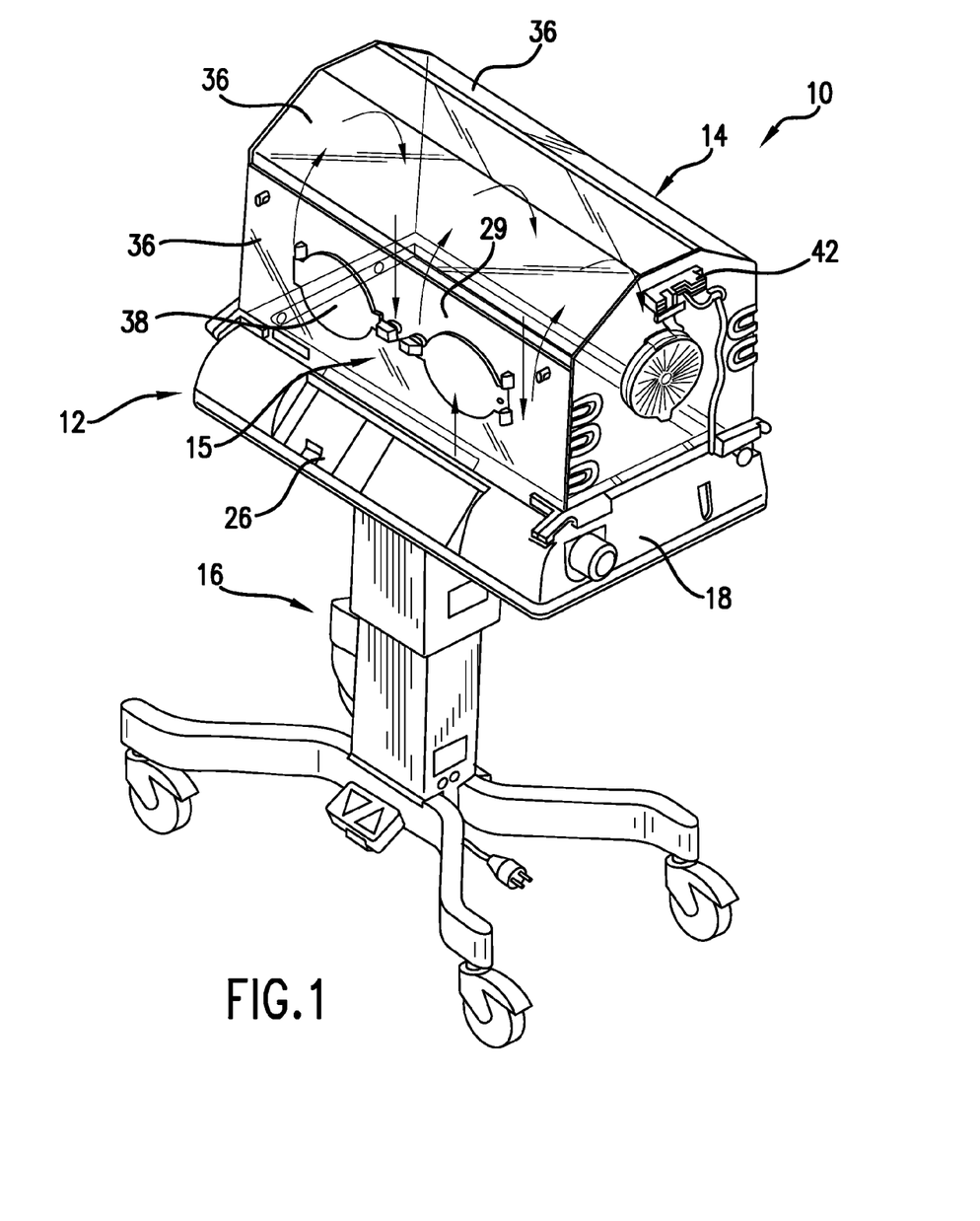
FIG. 1 is a perspective view of a warming therapy device according to a first exemplary embodiment of the present invention, including a base and a hood enclosing the base.
Figure 2:
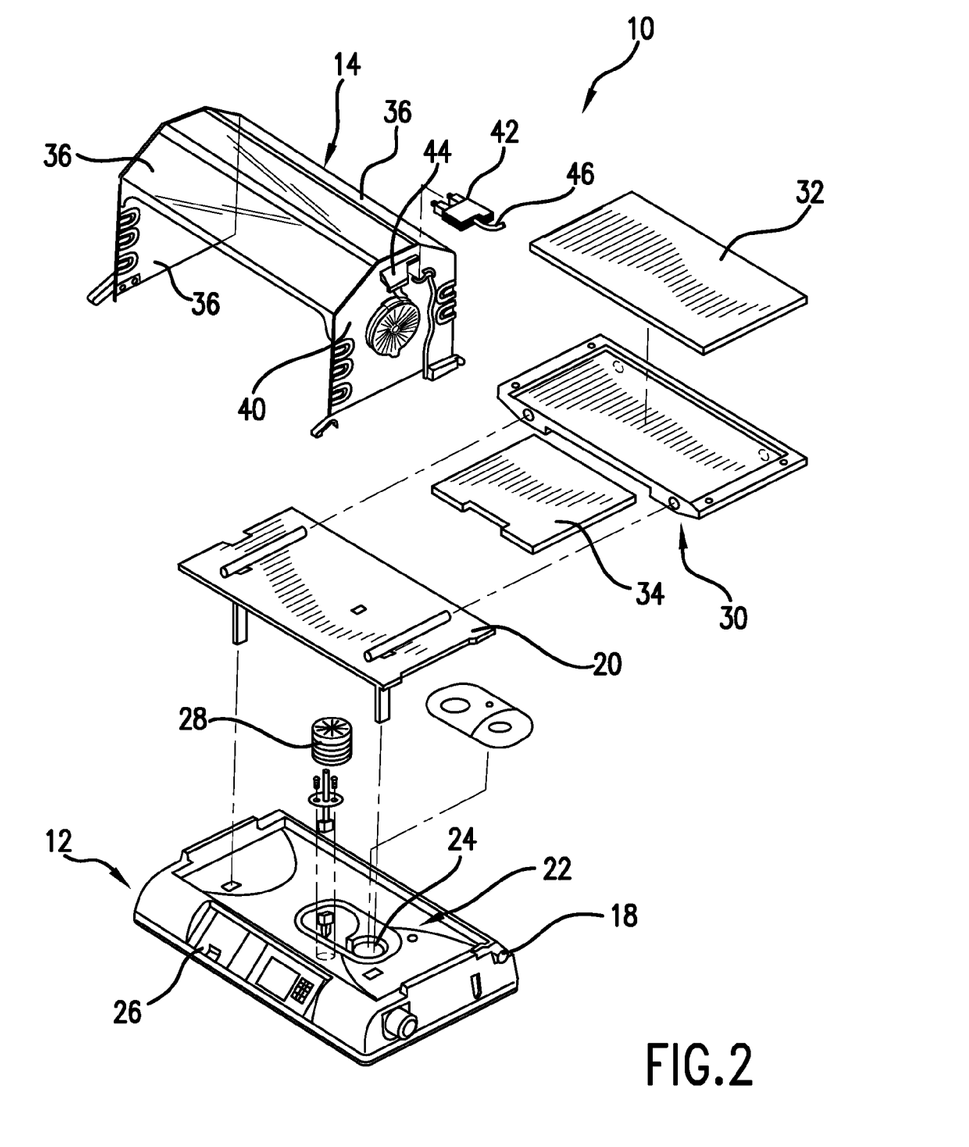
FIG. 2 is an exploded perspective view of the base and hood of the warming therapy device shown in FIG. 1 with a sidewall of the hood removed for clarity.

Closed care warming therapy devices (e.g., incubators) provide physical separation between the environment where the infant patient is disposed and the surrounding ambient air. This separation is typically provided by a hood or similar member which encloses the infant patient therein. This encapsulation of the infant patient facilitates creation of conditions favorable for the infant patient's development. Often times, the conditions inside the hood can be significantly different from those present in the ambient environment. Conditions inside the hood may be determined by varying the temperature level, humidity and/or oxygen concentration within the closed care environment, all of which can be controlled automatically using sensors integrated in the warming therapy device. For example, the temperature within the closed care environment may be controlled by sensing the skin temperature of the infant patient and making appropriate adjustments. FIGS. 1 and 2, discussed below, show an exemplary close care warming therapy device.

Alternatively to closed care warming therapy devices, open care devices (e.g., heaters or warmers) supply heat (through, e.g., overhead infrared radiation) to the infant patient to promote development, and do not typically utilize a hood which separates the infant patient from the surrounding environment. The amount of heat supplied to the infant patient may be fixed, or controlled by one or more skin temperature sensors coupled to the patient, as noted above.

FIGS. 1 and 2 show a warming therapy device 10 according to a first exemplary embodiment of the present invention. The warming therapy device 10 includes a base 12 and a hood 14 which combine to form an enclosure, or incubation chamber 15, within which an infant can be received. The base 12 includes a pedestal 16, a main housing 18 and a deck 20 having an upwardly facing surface. The deck 20 and main housing 18 are configured to provide a plurality of apertures communicating with a below deck ducting 22. Base 12 includes an air conditioning system that includes a fan 24, air filter (not shown), humidifier module 26, oxygen source (not shown) and a heater 28 communicating with the below deck ducting 22.

The illustrated warming therapy device 10 also includes an in-bed patient scale 30 configured to support a mattress 32 above an x-ray tray 34. The hood 14 includes a plurality of transparent walls 36 formed to include doors and portals 38 for access to an infant held within the enclosure. In the illustrated embodiment, an end wall 40 is formed with an aperture 44 for mounting a sensor module 42 therein.

The sensor module 42 may include a number of sensors, such as temperature, humidity, and oxygen level sensors. In particular, the humidity sensing portion of the sensor module 42 is adapted to detect the humidity level within the incubation chamber 15 and provide a signal to the humidifier module 26 through a data feed line 46.

Figure 3:
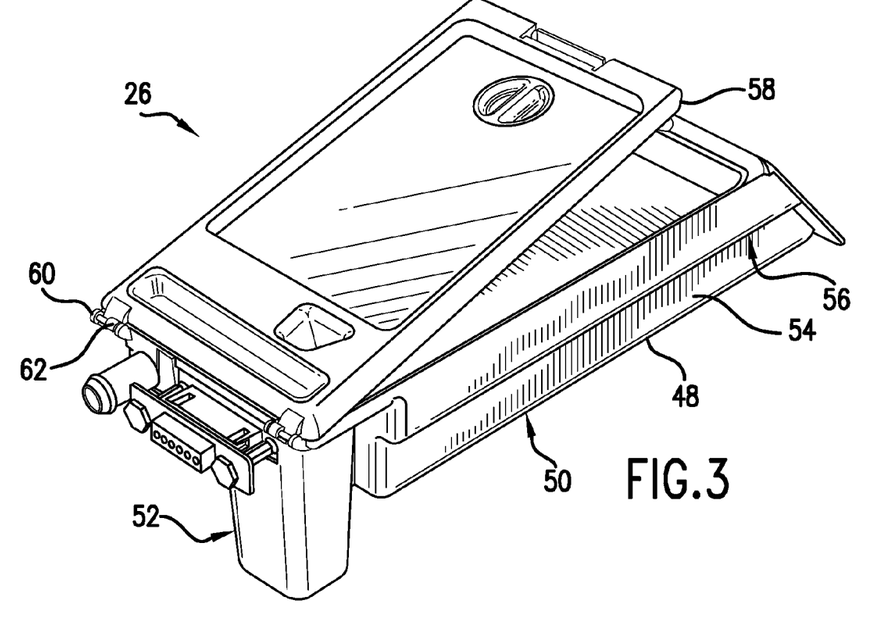
FIG. 3 is a perspective view of a humidifier module according to a first exemplary embodiment of the present invention.
Figure 4:
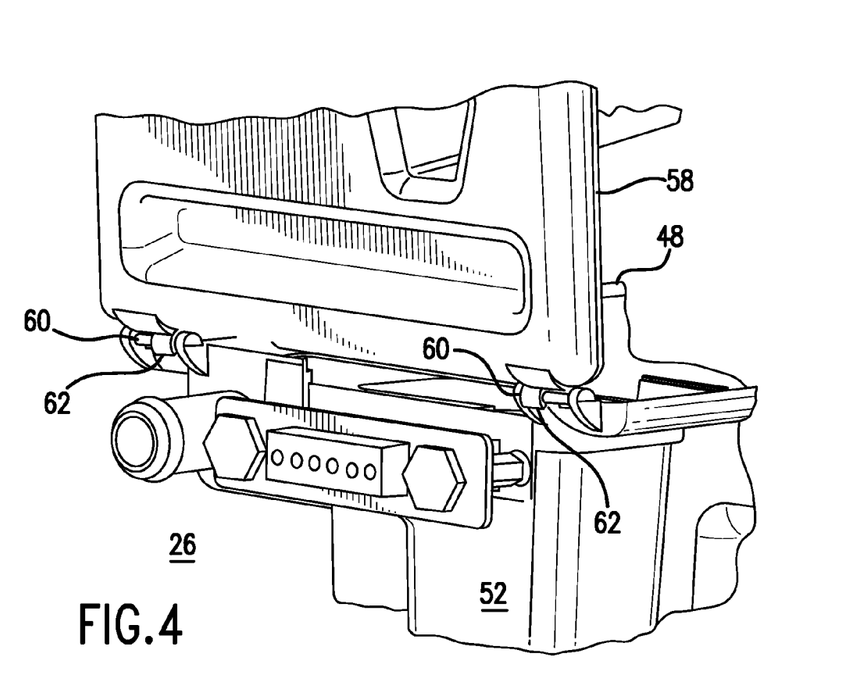
FIG. 4 is a detail perspective view of the humidifier module shown in FIG. 3, showing exterior details of a cover.

Referring now to FIG. 3, the humidifier module 26 has a reservoir body 48 defining a main reservoir 50 and an evaporator reservoir 52. The reservoir body 48 has sidewalls 54 with a shoulder relief 56 to facilitate sliding of the humidifier module 26 into the housing 18 of the base 12. The shoulder relief 56 rests on corresponding tracks (not shown) disposed within the base 12. The humidifier module 26 may be positioned within the base 12, such that the portion of the main reservoir 50 proximate the evaporator reservoir 52 is below the portion of the main reservoir 50 distal the evaporator reservoir 52, so as to assist the flow of water from the main reservoir 50 into the evaporator reservoir 52. The evaporator reservoir 52 may have ribs (not shown) protruding outwardly from the reservoir body 48. The ribs will serve to protect users from touching hot surfaces, such as the evaporator reservoir portion 52 of the reservoir body 48. Those of ordinary skill in the art will realize that the reservoir body 48 and cover 58 may be made of a number of materials such as plastics, acrylics or metals. The reservoir body 48 may be made transparent, translucent or tintable to allow for a visual assessment of reservoir conditions, including content, performance and cleanliness.

As will be appreciated by those of ordinary skill in the art, the open design of the humidifier module 26, as well as the fact that the cover 58 and other elements thereof may be easily removed, provides for relatively straightforward cleaning of the module. Cleaning of the humidifier module 26 is key to maintaining a sterile and hygienically-sound environment for the patient (e.g., infant). For example, if the humidifier module 26 is used for a time without cleaning, contaminants may build up in the reservoir body 48, which may be communicated to the patient through the air circulation system of the warming therapy device. The open design of the humidifier module 26, however, permits the reservoir body 48 to be removed and placed in an autoclave for cleaning. Once cleaning has been accomplished, the cover 58 may be reattached to the reservoir body 48, the heater assembly 84 (explained below) replaced, and the entire humidifier module 26 inserted into the main housing 18 of the base 12 for further operation.

Referring now to FIGS. 3-6, a cover 58 may be mated to the reservoir body 48 by hinges 60. The hinges 60 may include stop ribs 62 to limit the range of rotation that the cover 58 may pivot about the hinges 60. In the exemplary embodiment shown, the range of motion "R" is between 0 degrees (i.e., a closed position) and 95 degrees (i.e., the open position shown in FIGS. 4-6). The hinges 60 are constructed to releasably secure the cover 58 to the reservoir body 48. Particularly, the cover 58 may be coupled to the reservoir body 48 by friction-fit or snap-fit hinges, or other equivalent means known to those of ordinary skill in the art. Providing a removable cover 58 aids in maintenance and cleaning of the humidifier module 26 by making it easier to position the humidifier module 26 in a cleaning device, such as an autoclave. The reservoir body 48 may also include a channel 70 extending between the main reservoir 50 and evaporator reservoir 52 to allow water to flow to the evaporator reservoir 52 from the main reservoir 50. The channel 70 may be defined by sidewalls 72 and a floor 74. The reservoir body 48 may also include a mating groove 82, which cooperates with a downwardly extending tab 80 on the cover 58 to seal to cover with the reservoir body, as explained below.

Figure 5:
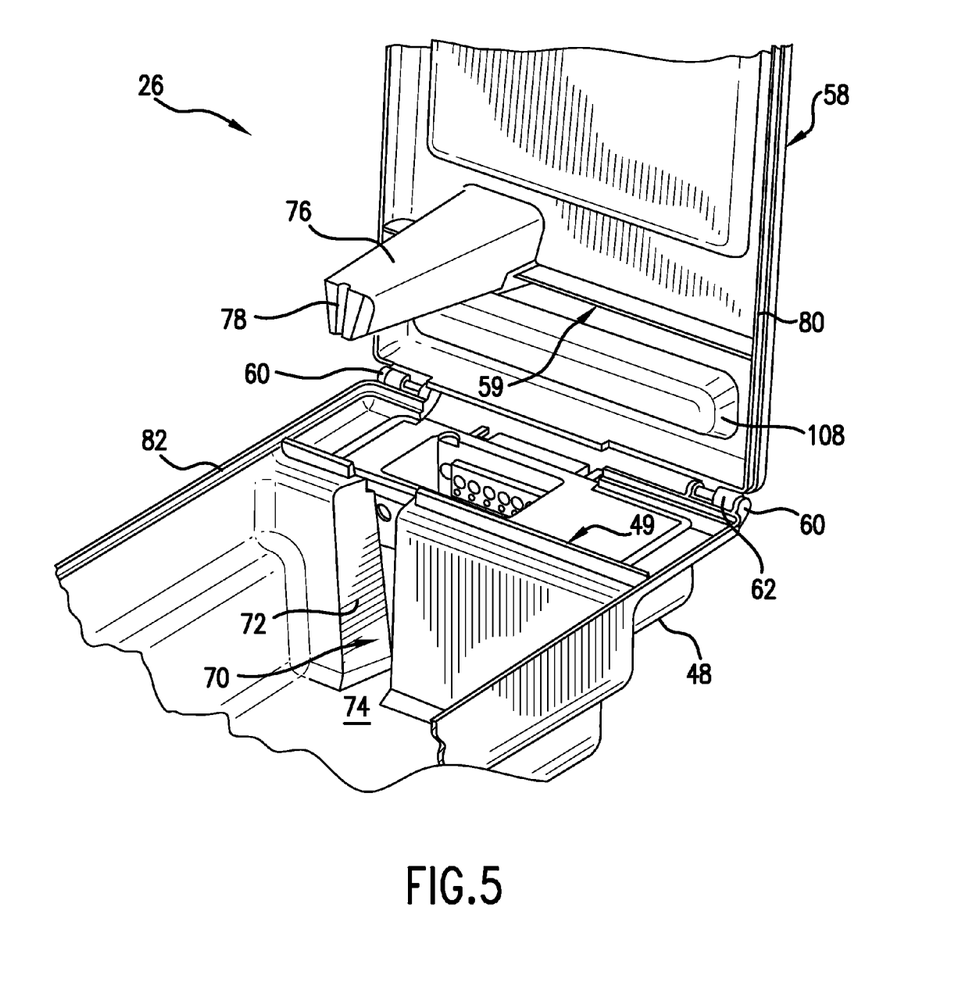
FIG. 5 is a detail perspective view of the humidifier module shown in FIG. 3, showing interior details of a cover.
Figure 14:
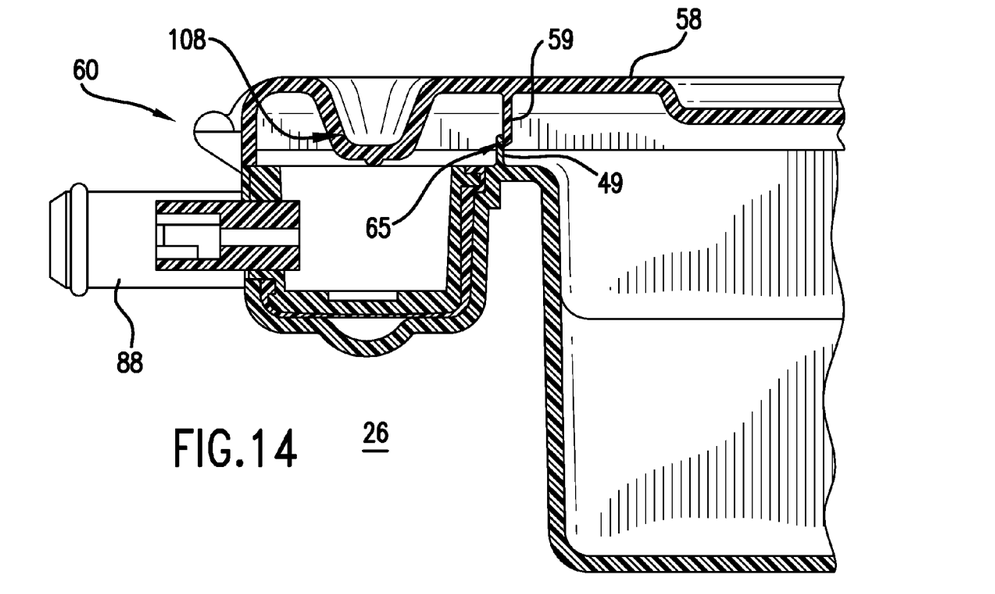
FIG. 14 is a side elevation view, in partial cross-section, of a portion of the humidifier module shown in FIG. 3.

As shown in FIG. 5, the reservoir body 48 may include a barrier wall 49, which is adapted to mate with a barrier wall 59 disposed on the cover 58, to form a water barrier between the main reservoir 50 and the evaporator reservoir 52. As shown in FIG. 14, the barrier wall 59 of the cover 58 overlaps the barrier wall 49 of the reservoir body 48 when the cover is disposed in a closed position, thereby creating a lap joint 65 at the point of contact. This lap joint 65 substantially prevents water in the main reservoir 50 from spilling over the top and into the evaporator reservoir 52 when the cover 58 is in a closed position. Therefore, when the cover 58 is closed, the only means for water to move from the main reservoir 50 to the evaporator reservoir 52 is through the slot 78 in the hollow post 76, described in further detail below. The cover 58 may also include a heater lock protrusion 108 for locking a heater unit in place, as described below.

Referring now to FIGS. 5-8, the cover 58 may include a latch 64 to secure the cover 58 in a closed position. The latch 64 may comprise a resiliently molded tab that may be positioned to engage a mating recess or tab (not shown) disposed on the reservoir body 48. Additionally, the reservoir body 48 may include a finger recess 66 positioned adjacent the latch 64 for opening the cover 58. A downwardly extending tab 80 may be located around the perimeter of the cover 58, and used for sealing the humidifier module 26. The tab 80 is sized to fit within a mating groove 82 located on the upper perimeter of the reservoir body 48, providing a tongue and groove fit between the cover 58 and reservoir body 48 to minimize spillage of water within the reservoir body 48 when the cover 58 is closed. The cover 58 may also include a removable fill cap 94 which may be adapted to permit filling of the main reservoir 50 without opening of the cover 58. Further, the cover 58 may include a recessed overflow tray 104 to contain water that may be spilled during filling using the opening underlying the fill cap 94.

Figure 6:
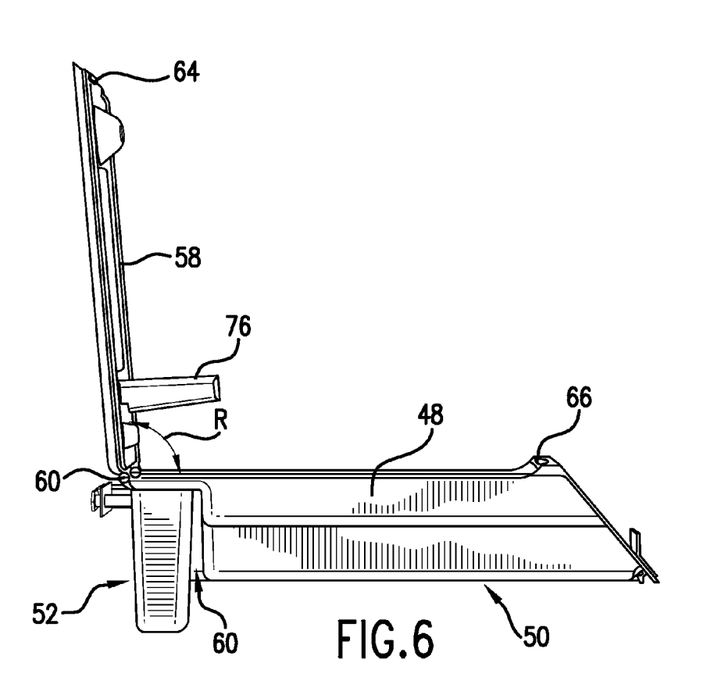
FIG. 6 is a side elevation view of the humidifier module shown in FIG. 3.
Figure 7:
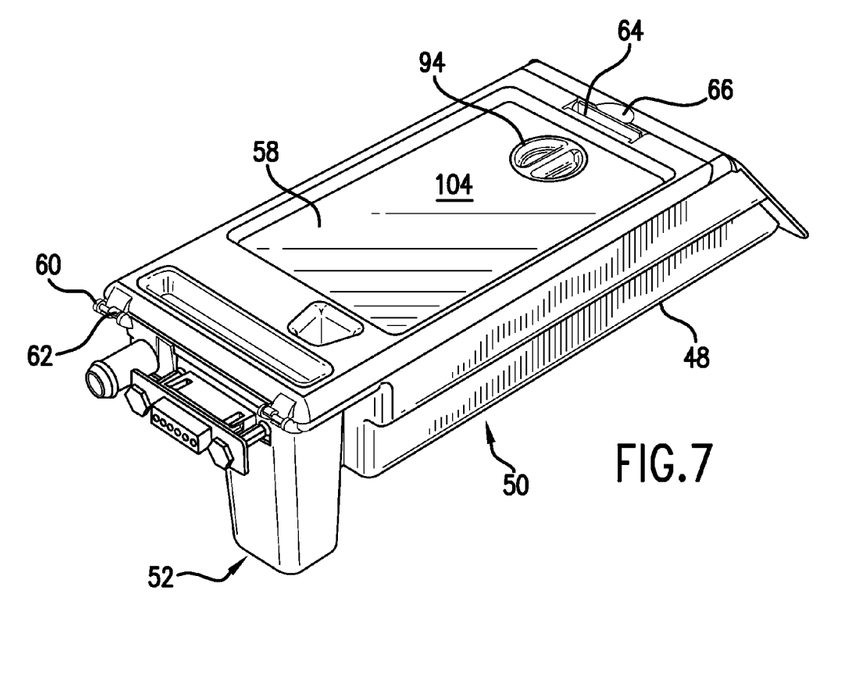
FIG. 7 is a perspective view of the humidifier module shown in FIG. 3, with the cover in a closed position.
Figure 9:
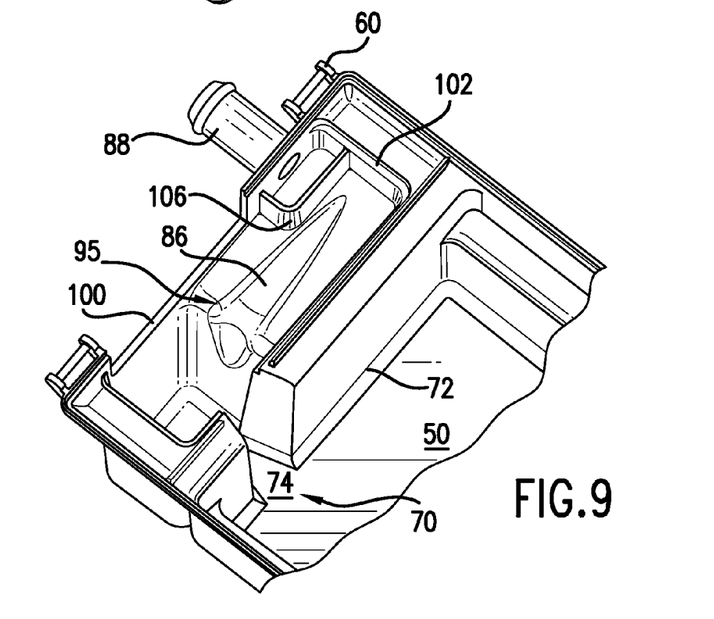
FIG. 9 is a top view of the humidifier module shown in FIG. 3, with the cover portion and heater removed to show interior details of the main reservoir.

Referring now to FIG. 6, there may be created a hollow air barrier 68 between the main reservoir 50 and the evaporator reservoir 52. The air barrier 68 is defined by the walls of the main reservoir 50 and the evaporator reservoir 52. As shown in FIG. 5, a channel 70 extends between the main reservoir 50 and evaporator reservoir 52 to allow water to flow to the evaporator reservoir 52 from the main reservoir 50. The channel 70 is defined by sidewalls 72 and a floor 74. The floor 74 is preferably at or slightly below the bottom of the main reservoir 50, to facilitate flow from the main reservoir 50 through the channel 70. The sidewalls 72 extend upwardly from the floor 74 and, as best seen in FIG. 9, are angled such that the opening of the channel 70 proximate the main reservoir 50 is wider than the opening of the channel 70 proximate the evaporator reservoir 52.

A hollow post 76 extends downwardly from the cover 58 and is sized to fit within the channel 70, further defining the air barrier 68 between the main reservoir 50 and the evaporator reservoir 52. The post 76 is wedge shaped, with angled walls sized to mate with the sidewalls 72 of the channel 70 to restrict the flow of water between the sidewalls 72 and the post 76. When the cover 58 is closed, the hollow post 76 may be biased against the sidewalls 72, forming a tight fit between the sidewalls 72 and hollow post 76. The air space between main reservoir 50 and evaporator reservoir 52 helps to insulate the evaporator reservoir 52, thereby reducing the energy required to generate steam by minimizing heat loss into the main reservoir 50.

On the bottom surface of the post 76, a slot 78 extends between the main reservoir 50 and the evaporator reservoir 52. Together with the floor 74 of the channel 70, the slot 78 defines a passageway that allows water to flow into evaporator reservoir 52. As water is evaporated from the deeper evaporator reservoir 52, water from the main reservoir 50 flows via gravity through the passageway to replace the evaporated water and maintain a sufficient level of water in the evaporator reservoir 52. By defining the passageway with the slot 78 and floor 74 of the channel 70, the passageway can be easily cleaned and obstructions can be easily removed when the cover 58 is opened. Use of a two-part passageway also allows for the use of a smaller passageway, thereby reducing the flow rate of water into the evaporator reservoir 52. This flow provides for more consistent evaporation and less fluctuation in temperature within the evaporator reservoir 52.

Figure 8:
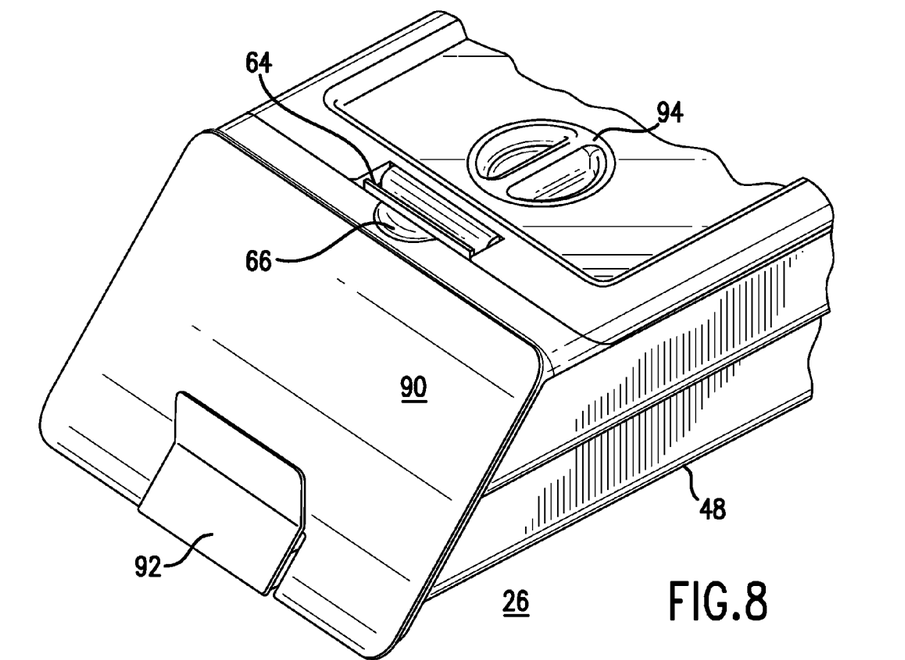
FIG. 8 is a detail perspective view of the humidifier module shown in FIG. 3, showing exterior details of a front panel and latch.

Referring now to FIG. 8, the humidifier module 26 may include an angled front panel 90 that may be sized and shaped to flushly fit with the housing 18 of the base 12 when the humidifier module 26 is disposed within the warming therapy device 10. The front panel may include a latch 92 for releasably securing the humidifier module 26 within the warming therapy device 10. The latch 92 may have a torsion spring biased to keep latch 92 in a locking position. The front panel 90 may have a viewing window or level indicator (not shown) to allow monitoring of water level inside the main reservoir 50. Alternatively, the front panel 90 may be transparent, or provide some other indication of the water level in the main reservoir 50.

Figure 15:
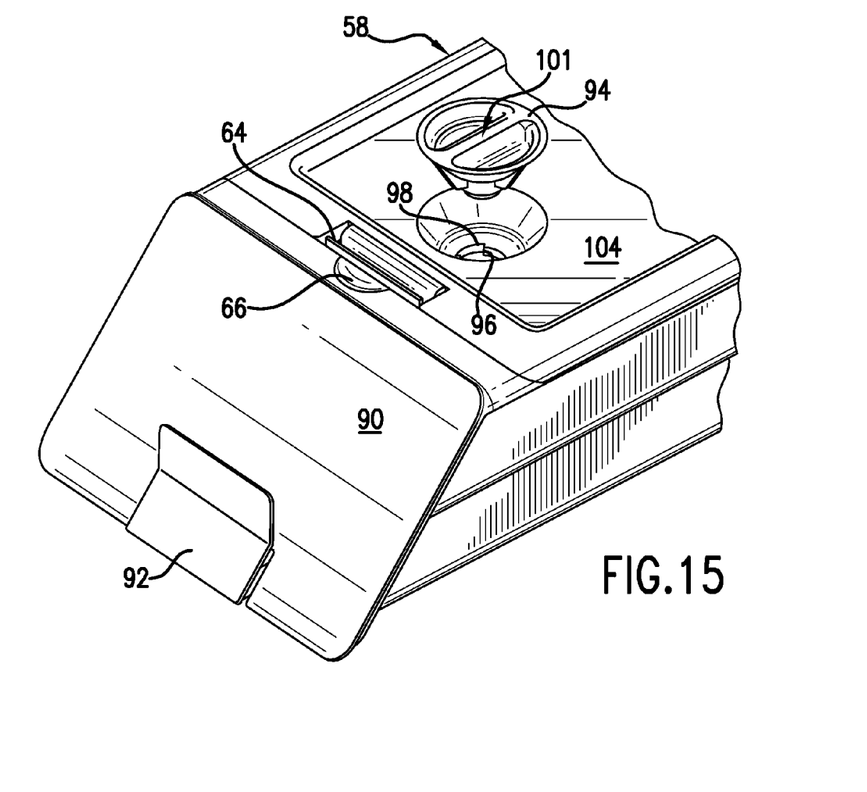
FIG. 15 is a detail perspective view of the humidifier module shown in FIG. 3, with a fill cap partially removed.
Figure 16:
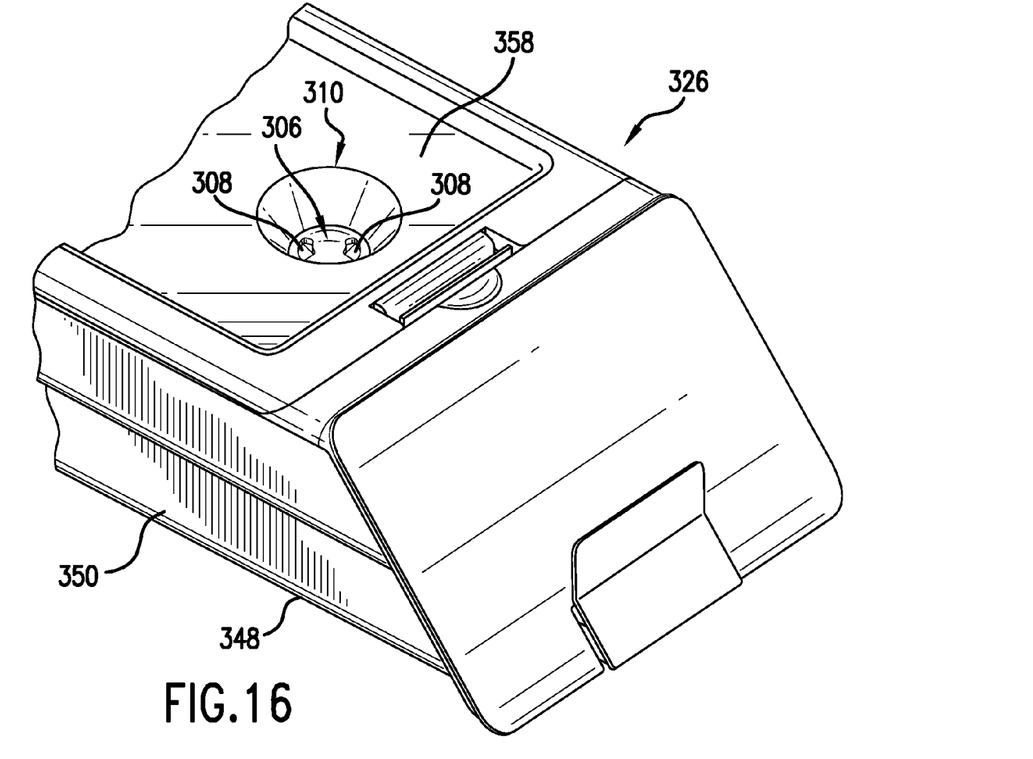
FIG. 16 is a detail perspective view of a humidifier module according to a third exemplary embodiment of the present invention, including an alternate fill cap.
Figure 17:
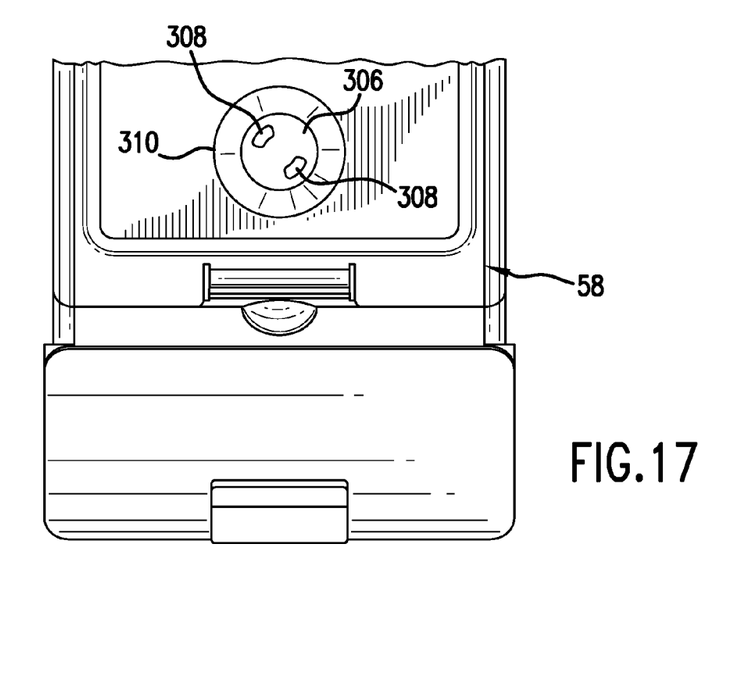
FIG. 17 is a top detail plan view of the humidifier module shown in FIG. 16.

Referring now to FIG. 15, the cover 58 may include a removable fill cap 94 to facilitate filling of the main reservoir 50 without opening of the cover 58. The fill cap 94 may be sized to releasably lock into a fill port 96 located on the cover 58. The fill cap 94 may be locked into the fill port 96 using a quarter turn tab that fits through a widened portion 98 of the fill port 96. Once the fill cap 94 is inserted into the fill port 96, the fill cap 94 may be rotated 90 degrees to lock the fill cap 94 in place. A handle 101 may extend across the center of the top side of the fill cap 94 to facilitate gripping and turning of the fill cap 94. The fill port 96 may be disposed within a sunken portion of the cover 58, and surrounded by a bevel. The level of the fill port 96 also serves as a visual indicator to help limit the amount of water that is poured into the main reservoir 58. As seen best in FIG. 7, the cover 58 may include a recessed overflow tray 104 to contain water that may be spilled during filling. The overflow tray 104 is preferably molded to facilitate water flow towards the fill port 96 and fill cap 94 when the humidifier module 26 is level.

Figure 10:
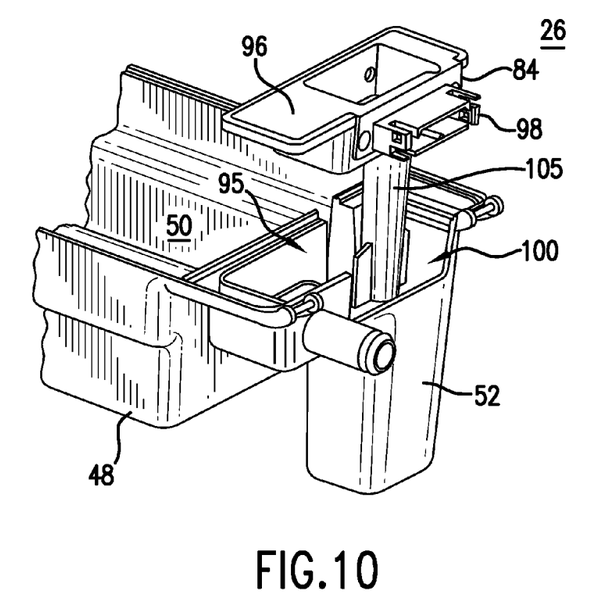
FIG. 10 is a detail perspective view of the humidifier module shown in FIG. 3, with a heater module partially removed.

Referring now to FIGS. 9 and 10, a heater assembly 84 may be removably secured within the evaporator reservoir 52. The heater assembly 84 may be secured into place by the cover 58 when the cover 58 is in a closed position, or by some other releasable means. Removing the heater assembly 84 for service allows the remainder of the humidifier module 26 to be cleaned using an autoclave. The heater assembly 84 heats water within the evaporator reservoir 52, thereby generating steam which flows upwardly through an undercut, such as a steam channel 86, out a discharge port 88 and ultimately into the air circulation system of the warming therapy device 10. Between the steam channel 86 and the discharge port 88 is a baffle 106 positioned in the flowpath of steam leaving the evaporator reservoir. The steam channel 86 and baffle 106 prevent water bubbles from exiting the evaporator reservoir 52 and entering the patient environment.

The heater assembly 84 may be constructed so as to be self-aligning within the evaporator reservoir 52. A heater cavity 95 may be formed in the top of the evaporator reservoir 52. The heater may include a top flange 96 that is adapted to mate with the heater cavity 95. A power and control contact 98 may extend laterally from the top flange 96, through a cutout 100 provided in the reservoir body 48, adjacent the heater cavity 95. The heater cavity 95 may also include a ledge 102 adapted to engage the top flange 96 and suspend the heater assembly 84 within the evaporator reservoir 52. A heater element 105 may extend downwardly from the top flange 96, into the lower portion of the evaporator reservoir 52.

Referring now to FIG. 5, in connection with FIGS. 9 and 10, the heater assembly 84 may be locked into place while the cover 58 is closed. Locking of the heater assembly 84 occurs when a heater lock protrusion 108 engages the upper surface of the top flange 96 of the heater assembly 84. The location of the heater lock protrusion 108 near the hinges 60 provides a lever to assist in providing pressure holding the heater assembly 84 in place. When the cover 58 is opened, the release of this hold down allows easy removal of the heater assembly 84 for cleaning.

Figure 11:
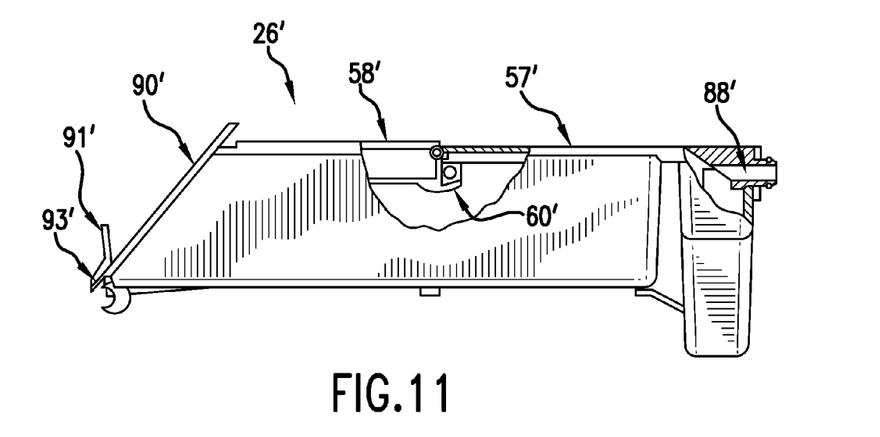
FIG. 11 is a side elevation view, in partial cross-section, of a humidifier module according to a second exemplary embodiment of the present invention.

Referring now to FIG. 11, a humidifier module 26' according to a second exemplary embodiment of the present invention is shown and described. The humidifier module 26' is similar to the humidifier module 26 in many respects, and like reference numerals denote like elements.

Like the humidifier module 26, the humidifier module 26' includes an angled front panel 90' (like front panel 90), which may be sized and shaped to flushly fit with the housing of a warming therapy device. For example, the front panel 90' may be sized and shaped to fit within the housing 18 of the base 12 of the warming therapy device 10 according to the first exemplary embodiment of the present invention. However, unlike the humidifier module 26, the front panel 90' of the humidifier module 26' may include an integrated latch 91' that may be pivotally connected to the front panel 90' by a pin 93'. The latch 91' may be spring loaded, as described above with respect to latch 92 of the humidifier module 26. The latch 91' may be used to lock the humidifier module 26' securely within a warming therapy device (e.g., warming therapy device 10). The front panel 90' may also include a viewing window or level indicator (not shown) to allow monitoring of the water level inside the main reservoir 50'. Alternatively, the front panel 90' may be transparent, or provide some other indication of the water level in the main reservoir 50'.

The humidifier module 26' may be covered by a lid 57', which also comprises a cover 58'. The lid 57' may include an integrated discharge port 88' which can allow a steam connection only if the lid is present on the device. For example, if the lid 57' is not present on the humidifier module 26', or is placed improperly, steam generated within the water reservoir will be substantially prevented from exiting the module through the discharge port 88', and thus heated air will not traverse to the patient disposed on the mattress of the associated warming therapy device (e.g., mattress 32 of warming therapy device 10). The discharge port 88' may be adapted to provide the same functionality as the discharge port 88 mentioned above (with regard to the humidifier module 26); however, the discharge port 88' may be integrally formed with the lid 57', rather than the reservoir body 48'.

The cover 58' may be locked to the humidifier module 26', when the lid 57' is in a closed position, thereby keeping parts of the humidifier module 26' together when the humidifier module 26' is removed from the associated warming therapy device (e.g., warming therapy device 10). Also, the cover 58' may be permanently attached to the lid 57', thereby reducing the chance of accidental loss when the humidifier module 26' is removed from the warming therapy device. The lid 57' may be pivotally attached to the humidifier module 26' by a hinge 60', which facilitates opening of the lid. Although the hinge 60' is shown in the center of the humidifier module 26', those of ordinary skill in the art will realize that the hinge 60' may be positioned at various places along the length of the humidifier module 26'.

Referring now to FIGS. 16-21, a humidifier module 326 according to a third exemplary embodiment of the present invention is shown and described. The humidifier module 326 is similar to the humidifier modules 26 and 26' in many respects, and like reference numerals denote like elements.

Like the humidifier modules 26, 26', the humidifier module 326 includes a reservoir body 348 defining a main reservoir 350 and an evaporator reservoir (not shown). The humidifier module 326 also includes a cover 358 coupled to the reservoir body 348 by hinges (not shown). However, unlike the humidifier modules 26, 26', the humidifier module 326 includes a fill cap 306 including fill apertures 308 (as opposed to the fill cap 94 associated with the humidifier module 26) which is disposed within a recessed fill port 310.

Figure 18:
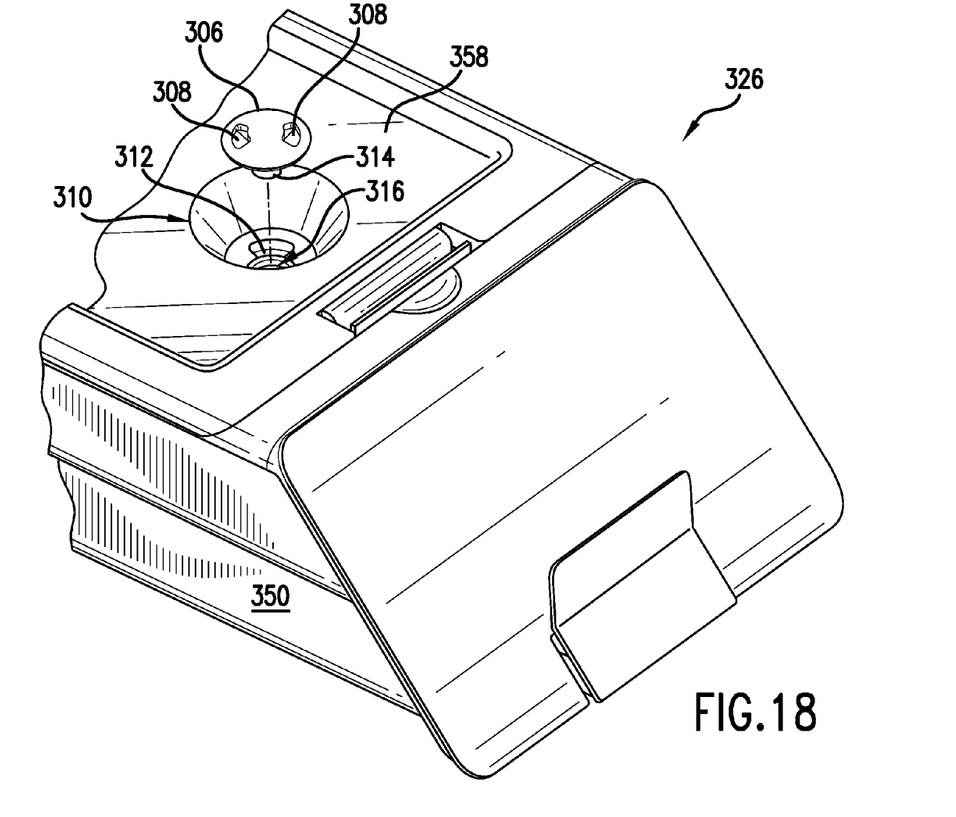
FIG. 18 is a detail perspective view of the humidifier module shown in FIG. 16, with the fill cap removed.
Figure 19:
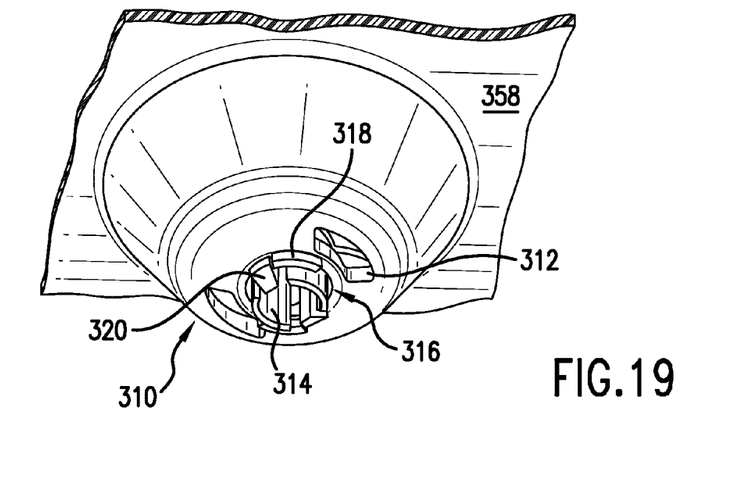
FIG. 19 is a detail perspective view of the underside of the cover of the humidifier module shown in FIG. 16, showing details of the fill cap.
Figure 20:
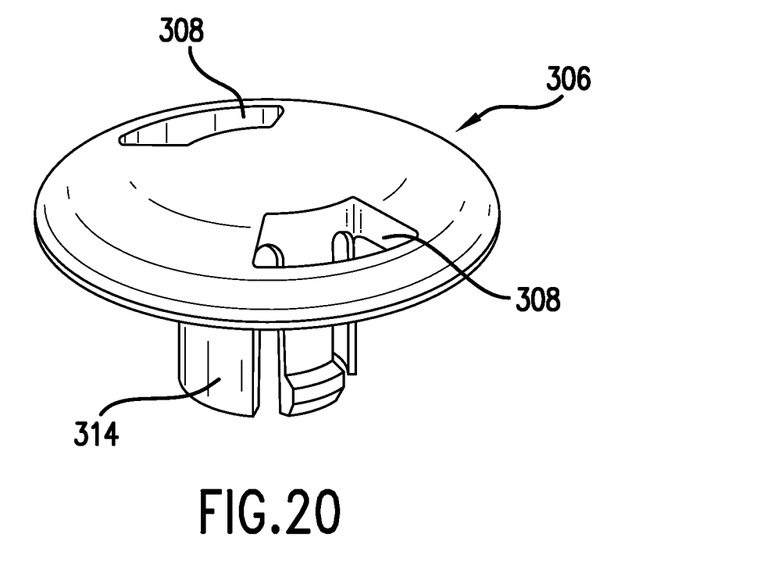
FIG. 20 is a detail perspective view of the fill cap shown in FIG. 18.
Figure 21:
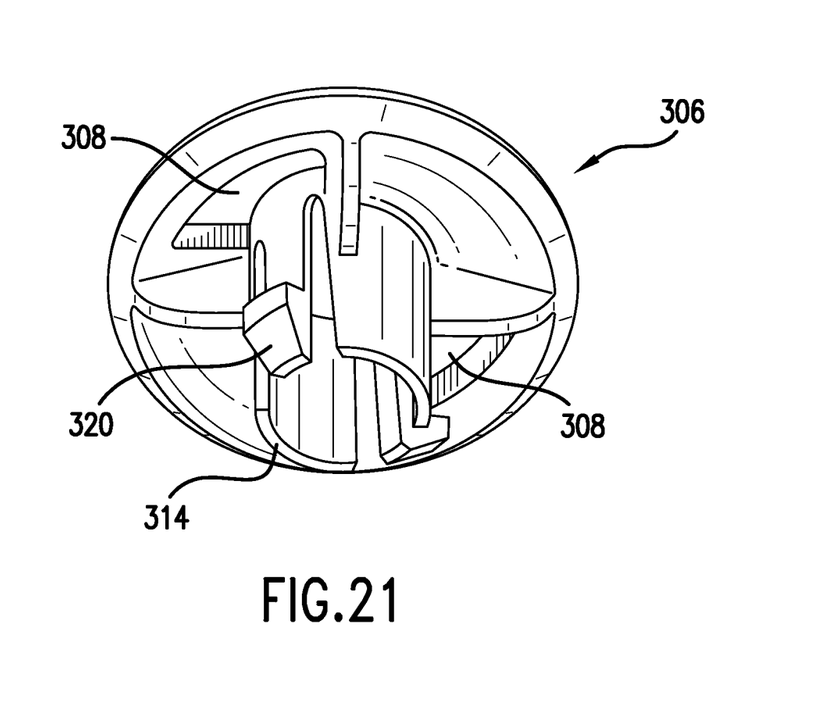
FIG. 21 is a detail perspective view of the underside of the fill cap shown in FIG. 20.

The fill cap 306 may include a round top section with at least two (2) fill apertures 308 extending therethrough. As best seen in FIG. 18, the fill port 310 formed in the cover 358 of the humidifier module 326 may include cover apertures 312 that are sized to match the fill apertures 308, such that when the fill apertures 308 are aligned with the cover apertures 312 a passageway into the main reservoir 50 is formed.

The fill cap 306 may also include a downwardly extending engagement post 314. The engagement post 314 is adapted to releasably secure the fill cap 306 within the fill port 310. The fill port 310 may also include an engagement aperture 316 sized to receive the engagement post 314 therein. On the underside of the fill port 310, two tabs 318 may border the engagement aperture 316. The engagement post 314 includes biased tabs 320, adapted to engage the underside of the fill port 310, for releasably locking the fill cap 306 within the fill port 310. In particular, the biased tabs 320 may be biased in a particular direction (e.g., inwardly or outwardly), such that when they are inserted into a corresponding aperture (e.g., engagement aperture 316), they become biased in the opposing direction for a short time until the tabs become sufficiently disposed within the aperture, at which time the tabs are biased back to their original position, to thereby hold the member attached thereto (e.g., fill cap 306) in place by friction-fit or snap-fit. The biased tabs 320 may be spaced to fit between the two tabs 318 of the fill port 310 to limit the rotation of the fill cap 306 within the fill port 310 to approximately 90 degrees. In such an exemplary embodiment as described above with regard to FIGS. 16-21, the fill cap 306 may be rotated to provide an opening to fill the main reservoir 350 without having to open the cover 358.

Figure 12:
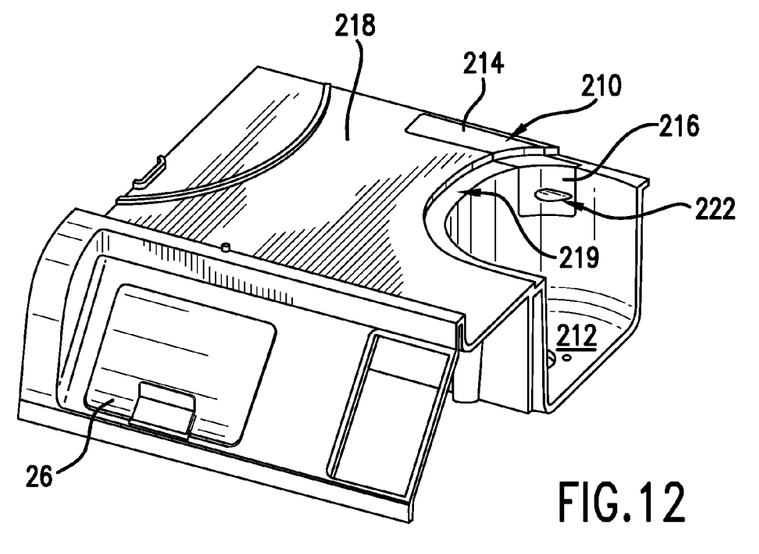
FIG. 12 is a perspective view of a warming therapy device base according to a second exemplary embodiment of the present invention.
Figure 13:
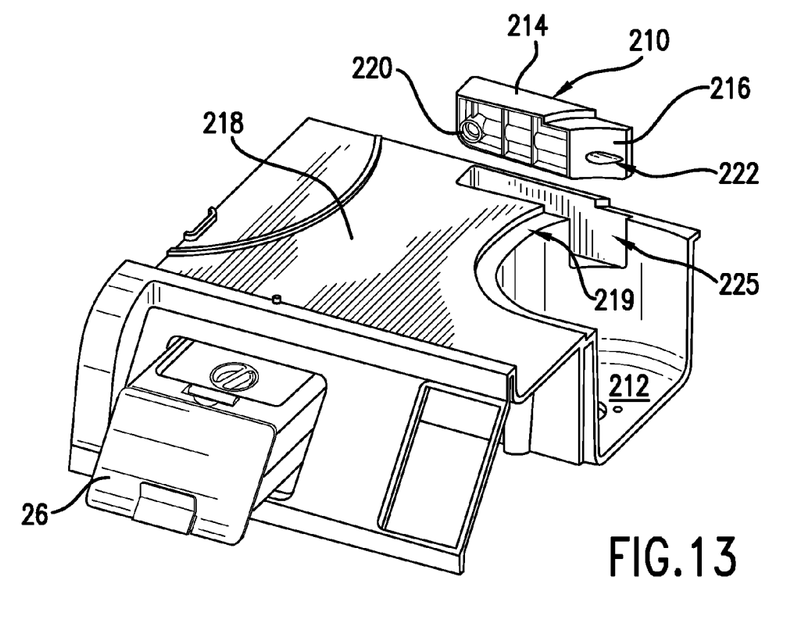
FIG. 13 is a perspective view of the warming therapy device base shown in FIG. 12, with a humidifier module and steam passage partially removed therefrom.

Referring now to FIGS. 12 and 13, there is shown a warming therapy device base 218 according to a second exemplary embodiment of the present invention. The base 218 is similar to the base 18 in many respects, and like reference numerals denote like elements. Those of ordinary skill in the art will realize that the base 218 may replace the base 18 of the warming therapy device 10 shown in FIGS. 1 and 2, and discussed above.

For instance, similar to the base 18, the base 218 may include a cavity 212 for housing a heater and fan (not shown, but similar to fan 24 and heater 26 in the base 18). However, alternatively from the base 18, the base 218 may include a removable steam passage 210, disposed adjacent the cavity 212, to provide a fluid connection means between the cavity 212 and a discharge port of the humidifier module (e.g., discharge port 88 of humidifier module 26). The steam passage 210 may be adapted to fit within a notch 225 in the base 218 and may be formed with a stepped upper surface 214, to flushly fit within a stepped area 219 of the base 218. The steam passage 210 may also be formed with a curved outer wall 216 to flushly fit with the rounded contours of the cavity 212. The steam passage 210 may also include an inlet 220, and an outlet 222 fluidly connected to the inlet 220. The inlet 220 may be located on the portion of the steam passage 210 closest to the humidifier module (e.g., humidifier module 26), and the outlet 222 may be located along the curved outer wall 216 of the steam passage, proximate the cavity 212 in the base 218.

As a result of the shaping of the steam passage 210, steam may be provided from the humidifier module (e.g., humidifier module 26) to the cavity 212, and onto the air conditioning system, with minimal disruption of airflow within the cavity 212. Because the steam passage 210 is made removable, it may be removed and inserted in an autoclave easily for cleaning and disinfecting. Although the base 218 is described above and shown in the associated figures for use with the humidifier module 26, those of ordinary skill in the art will realize that the base 218 may be used with the humidifier module 26', or any other suitable or equivalent humidifier module.

With all of the humidifier modules 26, 26', 326 discussed herein, the portion of the base 18 surrounding the humidifier modules 26, 26', 326 may include boundary surfaces sealing the microenvironment of the humidifier modules 26, 26', 326 (e.g., the chamber formed under the hood 14 where the patient is disposed) to substantially prevent other gases present in the microenvironment from leaking into the base 18, and vice versa, if any of the components of the humidifier modules 26, 26', 326 are misplaced by the end user. In addition to the protective boundary surfaces, a mechanical shutter (not shown) may be installed in the shell, matching the location of the discharge port 88, 88', further serving as a barrier to the microenvironment.

Furthermore, those of ordinary skill will be aware that the reservoir body 48, covers 58, 58' and lid 57' may be made of a number of materials such as plastics, acrylics or metals. The reservoir body 48 may be transparent, translucent or translucently-tinted to allow for a visual assessment of reservoir conditions, including content, performance and cleanliness. Viewing of the conditions within the humidifier modules 26, 26', 326 is beneficial from both a performance (e.g., to see cracks) and cleaning (e.g., to see through for viewing contaminants) standpoint.

Additionally, although the humidifier modules 26, 26', 326 according to the first and second exemplary embodiments are shown and described above with reference to an associated warming therapy device 10 of a specific configuration, those of ordinary skill in the art will realize that the humidifier modules 26, 26', 326 may be integrated into any suitable incubator, warmer, medical treatment device or other equivalent apparatus. Further, although the humidifier modules 26, 26', 326 are described above with reference to air or oxygen comprising the heated and circulated gas, those of ordinary skill in the art will realize that any gas may be heated (or cooled) and circulated using the humidifier modules 26, 26', 326 without departing from the scope of the present invention.

Although exemplary embodiments of the present invention have been described above for use in procedures involving infant patients, those of ordinary skill in the art will realize that the warming therapy device 10, and humidifier modules 26, 26', 326 according to the exemplary embodiments of the present invention, may be used for other types of operations and procedures, including for children and adults, without departing from the scope of the present invention.

Although the invention has been described in terms of exemplary embodiments, it is not limited thereto. Rather, the appended claims should be construed broadly to include other variants and embodiments of the invention which may be made by those skilled in the art without departing from the scope and range of equivalents of the invention. This disclosure is intended to cover any adaptations or variations of the embodiments discussed herein.

What is claimed is:

1. An apparatus comprising:
   a base for supporting a medical patient; and,
   a humidifier module removably coupled to the base, the humidifier module including a main reservoir and an evaporator reservoir separated by a channel,
   wherein the humidifier module further comprises a cover coupled to one of the main reservoir or the evaporator reservoir with a post extending outwardly therefrom, such that the post is disposed within the channel when the cover is closed, thereby creating a barrier from a flow of liquid from the main reservoir to the evaporator reservoir, and wherein the humidifier module comprises a reservoir body and wherein the cover is removably coupled to the reservoir body by one or more hinges, such that the main reservoir, the evaporator reservoir, and the channel are all disposed within the reservoir body.

2. The apparatus of claim 1, wherein the cover includes a first barrier wall extending outwardly therefrom, and the reservoir body includes a second barrier wall extending outwardly therefrom, such that when the cover is coupled to the reservoir body and closed, the first barrier wall overlaps the second barrier wall to form a lap joint.

3. The apparatus of claim 1, wherein the post includes a slot disposed therein which permits the flow of fluid between the main reservoir and the evaporator reservoir.

4. The apparatus of claim 1, wherein the cover includes a fill cap disposed therein.

5. The apparatus of claim 1, wherein the evaporator reservoir includes a steam channel for directing steam towards a discharge port.

6. The apparatus of claim 1, wherein the humidifier module further comprises a heater assembly.

7. The apparatus of claim 6, wherein the heater assembly includes a heater element which extends outwardly from the heater assembly into the evaporator reservoir.

8. An apparatus comprising:
a base for supporting a medical patient; and,
a humidifier module removably coupled to the base, the humidifier module including a main reservoir and an evaporator reservoir separated by a channel,
wherein the humidifier module further comprises a cover coupled to one of the main reservoir or the evaporator reservoir with a post extending outwardly therefrom, such that the post is disposed within the channel when the cover is closed, thereby creating a barrier from a flow of liquid from the main reservoir to the evaporator reservoir, and wherein the cover includes a latch for securing the cover to a portion of the main reservoir when the cover is closed.

9. An apparatus comprising:
a base for supporting a medical patient; and,
a humidifier module removably coupled to the base, the humidifier module including a main reservoir and an evaporator reservoir separated by a channel,
wherein the humidifier module further comprises a cover coupled to one of the main reservoir or the evaporator reservoir with a post extending outwardly therefrom, such that the post is disposed within the channel when the cover is closed, thereby creating a barrier from a flow of liquid from the main reservoir to the evaporator reservoir, and wherein the cover includes a hinge disposed substantially centrally along a length of the cover.

\* \* \* \* \*